US007144939B2

(12) United States Patent
Dotson et al.

(10) Patent No.: US 7,144,939 B2
(45) Date of Patent: *Dec. 5, 2006

(54) ORGANIC NUCLEATING AGENTS THAT IMPART VERY HIGH IMPACT RESISTANCE AND OTHER BENEFICIAL PHYSICAL PROPERTIES WITHIN POLYPROPYLENE ARTICLES AT VERY LOW EFFECTIVE AMOUNTS

(75) Inventors: Darin L. Dotson, Moore, SC (US); Brian M. Burkhart, Greenville, SC (US)

(73) Assignee: Milliken & Company, Spartanburg, SC (US)

( * ) Notice: Subject to any disclaimer, the term of this patent is extended or adjusted under 35 U.S.C. 154(b) by 214 days.

This patent is subject to a terminal disclaimer.

(21) Appl. No.: 10/632,208

(22) Filed: Jul. 29, 2003

(65) Prior Publication Data

US 2004/0132884 A1 Jul. 8, 2004

Related U.S. Application Data

(63) Continuation-in-part of application No. 09/820,569, filed on Mar. 29, 2001, now Pat. No. 6,599,971.

(51) Int. Cl.
*C08K 5/09* (2006.01)
*C07C 69/757* (2006.01)

(52) U.S. Cl. ............... 524/394; 524/396; 524/400; 560/116; 560/117; 560/118; 560/120; 560/125; 560/126; 560/127

(58) Field of Classification Search ............... 524/394, 524/396, 400; 560/116, 117, 118, 125, 126, 560/127, 120
See application file for complete search history.

(56) References Cited

U.S. PATENT DOCUMENTS

| | | | |
|---|---|---|---|
| 3,201,363 A | 8/1965 | Spurlin et al. ............. 260/30.4 |
| 3,207,736 A | 9/1965 | Wijga et al. ................ 260/93.7 |
| 3,207,739 A | 9/1965 | Wales ......................... 260/93.7 |
| 3,234,233 A | 2/1966 | Bolger et al. ............... 260/326 |
| 3,320,267 A | 5/1967 | Poos et al. .................. 260/295 |
| 3,367,926 A | 2/1968 | Voeks et al. ................ 260/93.5 |
| 3,527,736 A | 9/1970 | Averink et al. ............ 260/78.4 |
| 3,793,401 A | 2/1974 | Nield et al. ................. 260/876 |
| 3,829,450 A | 8/1974 | Schmerling et al. ..... 260/346.3 |
| 3,873,643 A | 3/1975 | Wu et al. .................... 260/878 |
| 3,882,194 A | 5/1975 | Krebaum et al. .......... 260/878 |
| 3,928,687 A | 12/1975 | Wada et al. ................. 428/461 |
| 3,933,779 A | 1/1976 | Baron et al. ............... 260/93.5 |
| 3,941,746 A | 3/1976 | Stephen et al. ............ 260/45.8 |
| 3,954,913 A | 5/1976 | Uebele et al. .............. 260/880 |
| 4,039,491 A | 8/1977 | Ikeda et al. ................. 260/875 |
| 4,134,895 A | 1/1979 | Roth et al. ................. 260/326 |
| 4,134,927 A | 1/1979 | Tomoshige et al. ......... 260/878 |
| 4,452,942 A | 6/1984 | Shida et al. ................. 525/74 |
| 4,476,184 A | 10/1984 | Lubowitz et al. ........... 428/288 |
| 4,503,219 A | 3/1985 | Reffert et al. ............... 528/481 |
| 4,704,421 A | 11/1987 | Teskin et al. ............... 524/287 |
| 4,739,017 A | 4/1988 | Tabor et al. ................ 525/300 |
| 4,778,837 A | 10/1988 | Waterman et al. ........... 524/89 |
| 4,801,637 A | 1/1989 | McCullough et al. ...... 524/287 |
| 4,829,114 A | 5/1989 | Trotoir et al. ............... 524/243 |
| 5,013,778 A | 5/1991 | Bath et al. .................. 524/173 |
| 5,135,975 A | 8/1992 | Rekers et al. ............... 524/108 |
| 5,491,187 A | 2/1996 | Ward et al. ................. 524/159 |
| 5,922,793 A | 7/1999 | Amos et al. ................. 524/159 |
| 5,929,146 A | 7/1999 | Amos et al. .................. 524/89 |
| 6,096,811 A | 8/2000 | Amos et al. .................. 524/89 |
| 6,156,836 A | 12/2000 | Iwanami et al. ............ 524/451 |
| 6,465,551 B1 * | 10/2002 | Zhao et al. ................. 524/284 |
| 6,534,574 B1 * | 3/2003 | Zhao et al. ................. 524/284 |
| 6,559,971 B1 * | 5/2003 | Watts et al. ................. 358/1.2 |
| 6,562,890 B1 * | 5/2003 | Dotson ....................... 524/396 |
| 6,599,971 B1 * | 7/2003 | Dotson et al. .............. 524/394 |
| 6,642,290 B1 * | 11/2003 | Dotson ....................... 524/108 |
| 6,703,434 B1 * | 3/2004 | Dotson ....................... 524/108 |
| 6,794,433 B1 * | 9/2004 | Dotson et al. .............. 524/241 |

FOREIGN PATENT DOCUMENTS

| | | | |
|---|---|---|---|
| DE | 1 544 851 | 5/1970 | |
| DE | 1 694 914 B | 3/1972 | |
| EP | 0267 695 | 5/1988 | |
| EP | 0336 573 | 3/1989 | |
| FR | 2 075 549 | 9/1971 | |
| FR | 2 656 620 | 7/1991 | |
| GB | 2 290 296 | 12/1995 | |
| JP | 53-40760 | 4/1978 | ................ 548/435 |
| JP | 57-18682 | 1/1982 | |

(Continued)

OTHER PUBLICATIONS

H.N. Beck, "Heterogeneous Nucleating Agents of Polypropylene Crystallization", Journal of Applied Polymer Science, vol. 11, pp. 673-685, 1967.

(Continued)

*Primary Examiner*—Kriellion Sanders
(74) *Attorney, Agent, or Firm*—Terry T. Moyer; John E. Vick, Jr.

(57) ABSTRACT

The use of organic based nucleating agents to induce certain specific polymer orientations into the molded polypropylene articles such that the resultant part has improved stiffness-impact properties without sacrificing other attributes of the polypropylene is provided. Such results have been obtained through the utilization of low amount of organic nucleating compounds, including, without limitation, specific metal salts of hexahydrophthalic acid (hereinafter HHPA). Furthermore, such nucleating compounds have been found to impart, again in such low added amounts, heretofore unforeseen levels of b-axis crystalline orientation which translates into improved physical properties as well.

10 Claims, No Drawings

FOREIGN PATENT DOCUMENTS

| | | |
|---|---|---|
| JP | 58-160343 | 9/1983 |
| JP | 60-13837 | 1/1985 |
| JP | 61-17834 | 5/1986 |
| JP | 01-180514 | 7/1989 |
| JP | 03-076815 A | 4/1991 |
| JP | 05-139460 | 6/1993 |
| JP | 07-173342 | 7/1995 |

OTHER PUBLICATIONS

Overman et al., "An Annual Publication of Satisfactory Methods for the Preparation of Organic Chemicals." Organic Synthesis, vol. 71, pp. 48-55, 1993.

Snider et al., "Mn(III)-Based Oxidative Free Radical Cyclization of Unsaturated Ketones," Journal of Organic Chemistry, vol. 60, pp. 5376-5377, 1995.

Fillon et al., "Self-Nucleation and Recrystallization of Isotactic Polypropylene (alpha Phase) Investigated by Differential Scanning Calorimetry," Journal of Polymer Science: Part B: Polymer Physics, vol. 31, pp. 1383-1393, 1993.

Fillon et al., "Self-Nucleation and Enhanced Nucleation of Polymers. Definition of a Convenient Calorimetric "Efficiency Scale" and Evaluation of Nucleating Additives in Isotactic Polypropylene (alpha phase)," Journal of Polymer Science: Part B: Polymer Physics, vol. 31 pp. 1395-1504, 1993.

\* cited by examiner

ORGANIC NUCLEATING AGENTS THAT IMPART VERY HIGH IMPACT RESISTANCE AND OTHER BENEFICIAL PHYSICAL PROPERTIES WITHIN POLYPROPYLENE ARTICLES AT VERY LOW EFFECTIVE AMOUNTS

CROSS REFERENCE TO RELATED APPLICATIONS

This application is a continuation-in-part of application Ser. No. 09/820,569, filed on Mar. 29, 2001 now U.S. Pat. No. 6,599,971.

FIELD OF THE INVENTION

This invention relates to the use of organic nucleating agents to induce certain specific polymer crystalline orientations into the molded polypropylene articles such that the resultant part has improved stiffness-impact properties without sacrificing other attributes of the polypropylene. Such results have been obtained through the utilization of low amounts of organic nucleating compounds, including, without limitation, specific cyclic dicarboxylates, including metal salts of hexahydrophthalic acid (hereinafter HHPA). Furthermore, such nucleating compounds have been found to impart, again in such low added amounts, heretofore unforeseen levels of b-axis crystalline orientation in molded articles which translates into improved physical properties as well.

BACKGROUND OF THE PRIOR ART

All U.S. patents cited below are herein fully incorporated by reference.

As used herein, the term "thermoplastic" is intended to mean a polymeric material that will melt upon exposure to sufficient heat but will retain its solidified state, but not prior shape without use of a mold or like article, upon sufficient cooling. Specifically, as well, such a term is intended solely to encompass polymers meeting such a broad definition that also exhibit either crystalline or semi-crystalline morphology upon cooling after melt-formation. Particular types of polymers contemplated within such a definition include, without limitation, polyolefins (such as polyethylene, polypropylene, polybutylene, and any combination thereof), polyamides (such as nylon), polyurethanes, polyesters (such as polyethylene terephthalate), and the like (as well as any combinations thereof).

Thermoplastics have been utilized in a variety of end-use applications, including storage containers, medical devices, food packages, plastic tubes and pipes, shelving units, and the like. Such base compositions, however, must exhibit certain physical characteristics in order to permit widespread use. Specifically within polyolefins, for example, uniformity in the orientation of polymer chains upon crystallization is a necessity to provide an effective, durable, and versatile polyolefin article. In order to achieve such desirable physical properties, it has been known that certain compounds and compositions provide nucleation sites for polyolefin crystal growth during molding or fabrication. Generally, compositions containing such nucleating compounds crystallize at a much faster rate than unnucleated polyolefin. Such crystallization at higher temperatures results in reduced fabrication cycle times and a variety of improvements in physical properties, such as, for example, stiffness.

Such compounds and compositions that provide faster and/or higher polymer crystallization temperatures are thus popularly known as nucleators. Such compounds are, as their name suggests, utilized to provide nucleation sites for crystal growth during cooling of a thermoplastic molten formulation. Generally, the presence of such nucleation sites results in a larger number of smaller crystals. As a result of the smaller crystals formed therein, clarification of the target thermoplastic may also be achieved, although excellent clarity is not always a result. The more uniform, and preferably smaller, the crystal size, the less light is scattered. In such a manner, the clarity of the thermoplastic article itself can be improved. Thus, thermoplastic nucleator compounds are very important to the thermoplastic industry in order to provide enhanced clarity, physical properties and/or faster processing.

As an example, dibenzylidene sorbitol derivatives are common nucleator compounds, particularly for polypropylene end-products. Compounds such as 1,3-O-2,4-bis(3,4-dimethylbenzylidene) sorbitol (hereinafter DMDBS), available from Milliken Chemical under the trade name Millad® 3988, provide excellent nucleation and clarification characteristics for target polypropylenes and other polyolefins. Other well known nucleator compounds include sodium benzoate, sodium 2,2'-methylene-bis-(4,6-di-tert-butylphenyl) phosphate (from Asahi Denka Kogyo K.K., known as NA-11), aluminum bis[2,2'-methylene-bis-(4,6-di-tert-butylphenyl)phosphate] (also from Asahi Denka Kogyo K.K., known as NA-21), talc, and the like. Such compounds all impart high polyolefin crystallization temperatures; however, each also exhibits its own drawback for large-scale industrial applications.

For example, of great interest is the compatibility of such compounds with different additives widely used within typical polyolefin (e.g., polypropylene, polyethylene, and the like) plastic articles. For instance, calcium stearate is a very popular acid neutralizer present within typical polypropylene formulations to protect the stabilizing additives (such as light stabilizers, antioxidants, etc.) from catalyst residue attack. Unfortunately, most of the nucleator compounds noted above also exhibit deleterious reactions with calcium stearate within polyolefin articles. For sodium, and other like metal ions, it appears that the calcium ion from the stearate transfers positions with the sodium ions of the nucleating agents, rendering the nucleating agents ineffective for their intended function. As a result, such compounds sometimes exhibit unwanted plate-out characteristics and overall reduced nucleation performance (as measured, for example, by a decrease in crystallization temperature during and after polyolefin processing). Other processing problems are evident with such compounds as well.

Other problems encountered with the standard nucleators noted above include inconsistent nucleation due to dispersion problems, resulting in stiffness and impact variation in the polyolefin article. Substantial uniformity in polyolefin production is highly desirable because it results in relatively uniform finished polyolefin articles. If the resultant article does not contain a well-dispersed nucleating agent, the entire article itself may suffer from a lack of rigidity and low impact strength.

Furthermore, storage stability of nucleator compounds and compositions is another potential problem with thermoplastic nucleators and thus is of enormous importance as well. Since nucleator compounds are generally provided in powder or granular form to the polyolefin manufacturer, and since uniform small particles of nucleating agents is imperative to provide the requisite uniform dispersion and performance, such compounds must remain as small particles through storage. Certain nucleators, such as sodium benzoate, exhibit high degrees of hygroscopicity such that the powders made therefrom hydrate easily resulting in particulate agglomeration. Such agglomerated particles may require further milling or other processing for deagglomeration in order to achieve the desired uniform dispersion within the target thermoplastic. Furthermore, such unwanted agglomeration due to hydration may also cause feeding and/or handling problems for the user.

These noticeable problems have thus created a long-felt need in the thermoplastic industry to provide nucleating/clarifying agents that do not exhibit the aforementioned problems and provide excellent peak crystallization temperatures for the target thermoplastics themselves, particularly with a wide variety of typical and necessary acid scavenger additives. To date, the best compounds for this purpose remain those noted above. Unfortunately, nucleators exhibiting exceptionally high peak crystallization temperatures, low hygroscopicity properties, excellent dispersion and concomitant clarity and stiffness, as well as compatibility with most standard polyolefin additives (such as, most importantly, calcium organic salt acid scavengers) have not been accorded the different thermoplastic industries. Such problems are not limited to polyolefins and are common within all thermoplastic applications in which nucleating agents are used.

Of greater particular concern and interest is the effect nucleators impart on polypropylene resins and articles made therefrom. Polypropylene is a semi-crystalline polymer valued for its low cost, low density, chemical resistance, and excellent stiffness but it suffers from inferior impact resistance. Polypropylene can be modified by a number of different routes to influence the final physical properties of the resin, especially the stiffness-impact balance. Generally, impact resistance can be improved by incorporation of a rubber phase into the polypropylene by either melt compounding or copolymerisation of other olefinic monomers such as ethylene, butylene or higher order olefins. These rubbery components phase segregate in these impact copolymer polypropylenes forming energy absorbing domains and increase the impact resistance of the resin at room temperature as well as very low temperatures, down to −30° C. or lower depending on the rubber content. However, these impact copolymers, which are widely available from most commercial polypropylene producers, suffer from significantly reduced strength and stiffness. Therein lies the problem with polypropylene; there is a fundamental trade-off between having high stiffness, which tends to decrease the impact resistance, and high impact, which tends to decrease the resin stiffness.

To overcome this issue, filling agents are used to modify the physical properties of polypropylene to increase stiffness. For example U.S. Pat. No. 6,156,836 describes a composite material comprised of highly specific combinations of polypropylene, rubber components (such as ethylene-propylene copolymer), and talc filler at 15–25% by weight in order to create a resin with improved stiffness-impact balance arising from a specific "b-axis" orientation of the crystals within molded parts. Furthermore U.S. Pat. No. 5,591,795 also describes a composite material comprised of highly specific combinations of polypropylene, rubber components (such as ethylene-propylene copolymer), and talc filler at 5–15% by weight, also for stiffness-impact benefits. The talc components in these inventions impart rigidity to the sample because of its inorganic nature and its ability to induce a highly specific "b-axis" orientation into the polypropylene. "B-axis" orientation occurs when the polypropylene crystals align in a specific orientation within the part such that the crystallographic "b-axis" of the polypropylene crystals aligns with the normal, or thickness, direction of the molded part, while the a and c axes are distributed about the machine and transverse directions.

However, such a method of blending together these components (polypropylene, rubber, filler) is not easily accomplished in every situation and suffers from the drawbacks of creating increased costs for the resin from the extra compounding steps needed to get thorough mixing and dispersion of all of the components, increased polymer density from the large mass fraction of inorganic fillers, loss of impact resistance, and furthermore these materials are completely opaque. An improved method of obtaining this effect would be to have a low density (organic), low usage-level nucleating agent that could impart a similar effect. This additive would primarily have an effect on the hompolymer fraction of the blend, either in an impact copolymer or a random copolymer. As evinced by the degrees to which the industry is seeking a solution to this stiffness-impact conundrum through the use of complex blends, the invention described herein can be used to overcome this problem.

OBJECTS OF THE INVENTION

Therefore, an object of the invention is to provide a nucleator compound and compositions thereof that exhibit excellent calcium stearate compatibility within target thermoplastic articles and formulations. A further object of the invention is to provide a thermoplastic nucleating agent that provides excellent high peak crystallization temperatures, for example, to polypropylene articles and formulations, and also exhibits extremely low hygroscopicity in order to accord an extremely good shelf-stable additive composition. Another object of the invention is to provide an easily dispersed nucleator compound such that said polyolefin exhibits very high stiffness and good clarity. Additionally, it is an object of this invention to provide a nucleator compound or composition which may be used in various thermoplastic media for myriad end-uses. A further object of this invention is to provide an organic nucleating compound for use in polypropylene, usable at low levels, less than 1% by weight, preferably less than 0.5% by weight, more preferably less than 0.2% by weight, that imparts a specific "b-axis" orientation to the polypropylene resin such that the molded part has both improved stiffness, as well as improved impact resistance, and thus an improved stiffness-impact balance.

Accordingly, this invention encompasses metal salts of a compound conforming to Formula (I)

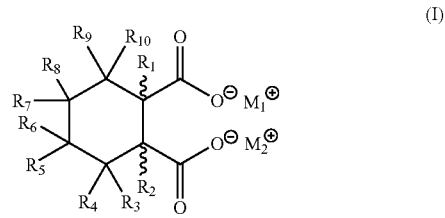

(I)

wherein $M_1$ and $M_2$ are the same or different and are selected from at least one Group I or Group II metal cation, preferably calcium, strontium, lithium, sodium and/or monobasic aluminum, and wherein $R_1$, $R_2$, $R_3$, $R_4$, $R_5$, $R_6$, $R_7$, $R_8$, $R_9$, and $R_{10}$ are either the same or different and are individually selected from the group consisting of hydrogen, $C_1$–$C_9$ alkyl [wherein any two vicinal (neighboring) or geminal (same carbon) alkyl groups may be combined to form a carbocyclic ring of up to six carbon atoms], hydroxy, $C_1$–$C_9$ alkoxy, $C_1$–$C_9$ alkyleneoxy, amine, and $C_1$–$C_9$ alkylamine, halogens (fluorine, chlorine, bromine, and iodine), and phenyl. The term "monobasic aluminum" is well known and is intended to encompass an aluminum hydroxide group as a single cation bonded with the two carboxylic acid moieties. Furthermore, form each of these potential salts, the stereochemistry at the asymmetric carbon atoms may be cis or trans, although cis is preferred.

Alternatively, this invention concerns an organic nucleating agent that induces b-axis orientation of the polypropylene crystals [as measured by relative angle (ND) in excess of 13.5, preferably higher], and/or induces a stiffness to impact balance ratio of at least 4.5, preferably higher, within a test homopolymer polypropylene formulation comprising said nucleating agent, wherein the unnucleated test homopolymer propylene exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 kpi, an Izod impact strength of about 0.67 ft-lb/in, and a deflection temperature at 0.46 mPa of about 93°, and wherein said formulation comprising said combination is extruded then molded into plaques having dimensions of about 51 mm×76 mm×3.00 mm, wherein said peak crystallization temperature is measured by differential scanning calorimetry in accordance with a modified ASTM Test Method D3417-99 at heating and cooling rates of 20° C./minute, wherein said haze measurements are performed in accordance with ASTM Standard Test Method D1003-61, and wherein the total amount of said additive composition within said test homopolymer is at most 0.25% by weight. Furthermore, articles comprising such organic nucleating agents are encompassed within this invention, as well as articles comprising cyclic dicarboxylate salt nucleating agents, wherein such nucleating agents exhibit low hygroscopicity, and said nucleating agents induce relatively high crystallization temperatures (at least 116° C.) within the same type of test homopolymer formulation as noted above. The term "organic nucleating agent" is intended to encompass any carbon-based compound that effectively functions as a nucleating agent for polypropylene.

It should also be well understood and appreciated by one of ordinary skill within this art that the inventive nucleating agent is defined above as performing to a certain degree within a test polymer formulation, and is not required to be a component within such a test polymer formulation. Thus, although such an inventive nucleating agent must perform to a certain level within a test homopolymer propylene, it may be present within any other type of polymer (such as a thermoplastic), including blends of polymers. The particular polymers within which such an inventive nucleating is effective and useful are listed below in greater detail.

DETAILED DESCRIPTION OF THE INVENTION

As noted above, in order to develop a proper thermoplastic nucleator for industrial applications, a number of important criteria needed to be met. The inventive calcium, strontium, monobasic aluminum, and lithium HHPA salts meet all of these important requirements very well. For instance, these inventive compounds do not hydrate readily and thus granular or powder formulations of such a salt do not agglomerate or clump together. The cost benefits from such shelf stability are apparent since there is little if any need to separate agglomerated powders upon introduction to thermoplastic processing equipment. Furthermore, as discussed in greater detail below, these inventive salts provide excellent high peak crystallization temperatures in a variety of polyolefin and polyester formulations, particularly within random copolymer polypropylene (hereinafter RCP), homopolymer polypropylene (hereinafter HP), impact copolymer polypropylene (hereinafter ICP), syndiotactic polypropylene (s-PP), polyethylene terephthalate (hereinafter PET), polyamides (such as nylons), and any combinations thereof. Additionally, such inventive salts provide high stiffness (modulus) characteristics to the overall final polyolefin product without the need for extra fillers and reinforcing agents. Lastly, and of great importance within the polypropylene industry, such inventive salts do not react deleteriously with calcium stearate co-additives. Such a property, combined with the other attributes, is highly unexpected and unpredictable.

Such inventive compounds thus provide excellent nucleating capability. Sodium salts of certain aromatic and cycloaliphatic carboxylic acids have been discussed within the prior art, most notably within U.S. Pat. No. 3,207,739 to Wales. Broadly disclosed, the patentee includes metal salts of a number of such compounds, most particularly sodium, although Group I and II metals are also broadly discussed. However, patentee specifically states that aromatic benzoates, in particular sodium benzoate, are the best compounds for polyolefin nucleation purposes. Furthermore, patentee mentions strontium as a cation for benzoate alone and specifically teaches away from the utilization of calcium salts due to heat processing problems. Additionally, patentee equates Group I and II metals as cations for his preferred benzoates; however, as discussed below in greater detail, it is evident that other Group II metals, such as magnesium and barium, are highly ineffective with HHPA as polyolefin nucleators. Lastly, it has now been found that in comparison with patentee's decidedly preferred sodium benzoate, the inventive compounds provide more beneficial properties, including, without limitation, less susceptibility to plate-out and blooming on the mold during polyolefin article formation, lower hygroscopicity, and again of greater importance, less reactivity with calcium stearate thereby permitting greater amounts of both compounds to function in their intended capacities within the target polyolefin formulation.

The inventive HHPA salts may thus be added within the target thermoplastic in an amount from about 0.01 percent to 2.0 percent by weight, more preferably from about 0.2 to about 1.5 percent, and most preferably from about 0.05 to 1.0 percent, in order to provide the aforementioned beneficial characteristics. It may also be desirable to include up to 50% or more of the active compound in a masterbatch, although this is not a restriction. Optional additives within the inventive HHPA salt-containing composition, or within the final thermoplastic article made therewith, may include plasticizers, stabilizers, ultraviolet absorbers, and other similar standard thermoplastic additives. Other additives may also be present within this composition, most notably antioxidants, antimicrobial agents (such as silver-based compounds, preferably ion-exchange compounds such as ALPHASAN® antimicrobials from Milliken & Company), antistatic compounds, perfumes, chlorine scavengers, and the like. These coadditives, along with the nucleating agents, may be present as an admixture in powder, liquid, or in compressed/pelletized form for easy feeding. The use of dispersing aids may be desirable, such as polyolefin (e.g., polyethylene) waxes, stearate esters of glycerin, montan waxes, and mineral oil. Basically, the inventive metal HHPA compounds may be present (up to 20% by weight or more) in any type of standard thermoplastic (e.g., polyolefin, most preferably) additive form, including, without limitation, powder, prill, agglomerate, liquid suspension, and the like, particularly comprising the dispersing aids described above. Compositions made from blending, agglomeration, compaction, and/or extrusion may also be desirable.

The term polyolefin or polyolefin resin is intended to encompass any materials comprised of at least one semicrystalline polyolefin. Preferred examples include isotactic and syndiotactic polypropylene, polyethylene, poly(4-methyl)pentene, polybutylene, and any blends or copolymers thereof, whether high or low density in composition. The polyolefin polymers of the present invention may include aliphatic polyolefins and copolymers made from at least one aliphatic olefin and one or more ethylenically unsaturated co-monomers. Generally, the co-monomers, if present, will be provided in a minor amount, e.g., about 10 percent or less or even about 5 percent or less, based upon the weight of the polyolefin. Such comonomers may serve to assist in clarity improvement of the polyolefin, or they may function to improve other properties of the polymer. Higher amounts of co-monomer (for instance, ethylene, e.g., 10–25% or more), may also be present in the polyolefin to engender greater impact resistance (hereinafter impact copolymer, or ICP's). Other polymers or rubber (such as EPDM or EPR) may also be compounded with the polyolefin. Other co-monomer examples include acrylic acid and vinyl acetate, etc. Examples of olefin polymers whose transparency and crystallization temperature can be improved conveniently according to the present invention are polymers and copolymers of aliphatic mono-olefins containing 2 to about 6 carbon atoms which have an average molecular weight of from about 10,000 to about 2,000,000, preferably from about 30,000 to about 300,000, such as, without limitation, polyethylene (PE), linear low density polyethylene (LLDPE), isotactic polypropylene (I-PP), syndiotactic polypropylene (s-PP), random copolymer polypropylene (RCP), crystalline ethylenepropylene copolymer (ICP), poly(1-butene), poly(4-methylpentene), poly(1-hexene), poly(1-octene), and poly(vinyl cyclohexene). The polyolefins of the present invention may be described as basically linear, regular polymers that may optionally contain side chains such as are found, for instance, in conventional, low density polyethylene. Although polyolefins are preferred, the nucleating agents of the present invention are not restricted to polyolefins, and may also give beneficial nucleation properties to polymers such as polyethylene terephthalate (PET), polybutylene terephthalate (PBT), and polyethylene naphthalate (PEN), as well as polyamides such as Nylon 6, Nylon 6,6, and others. Generally, any thermoplastic composition having some degree of crystalline content may be improved with the nucleating agents of the present invention.

The compositions of the present invention may be obtained by adding the inventive HHPA salt (or combination of salts or composition comprising such salts) to the thermoplastic polymer or copolymer and merely mixing the resultant composition by any suitable means. The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article.

The nucleated thermoplastic is intended to be utilized as, for instance and not by limitation, medical devices, such as pre-filled syringes for retort applications, intravenous supply containers, and blood collection apparati; food packages; liquid containers, such as for drinks, medicines, shampoos, and the like; apparel cases; microwaveable articles; shelves; cabinet doors; mechanical parts; automobile parts; sheet; pipes and tubes; rotationally molded products; blow-molded products; fiber (spun or nonwoven); compression molded products; basically any thermoplastic article wherein the effects of nucleation may be advantageous.

In terms of the physical property improvements imparted to polypropylene articles, such cyclic dicarboxylate nucleating agents as noted above, including Group I and/or Group II metal salts of hexahydrophthalate, cis- in configuration, preferably (although trans- may also provide such beneficial results, too), appear to provide the best overall desired results. In the past, as noted above, talc was the main stiffness enhancement ingredient, due to its high availability and low cost, primarily, within polypropylene articles. However, in order to achieve such high degrees of flexural modulus, very high amounts of such an additive were required, with a concomitant loss of impact strength. This addition of talc increased the weight of the target articles, as well, thereby translating into increased costs and complexities in manufacture, storage, and transport, at least. Thus, the ability to impart such desirable properties with minimal amounts of nucleating additives is highly unexpected in addition to the standard nucleation capabilities of such organic compounds (crystallization temperature increase, and the like).

PREFERRED EMBODIMENTS OF THE INVENTION

Examples of the particularly preferred polypropylene articles within the scope of the present invention and compositions thereof are presented below, with the production of the utilized nucleating additives presented first.

Production of Nucleator HHPA Salts

EXAMPLE 1 cis-Calcium HHPA

To an 8-L cylindrical kettle fitted with a mechanical paddle stirrer and thermometer was added water (4 L) and calcium hydroxide (481 g, 6.49 moles) with stirring at room temperature. To this slurry was added cis-hexahydrophthalic anhydride (1 kg, 6.49 moles) and the slurry was heated to 50° C. After stirring with heat for 5 hours, the mixture became quite thick, at which time the pH of the aqueous phase was found to be about 7. The white product was collected by suction filtration, washed with copious amounts of water, and dried in a vacuum oven overnight at 140° C. The dry weight was 1270 grams (93% yield) having a melting point greater than about 400° C. The IR and NMR spectra were consistent with the expected product.

EXAMPLE 2 cis-Strontium HHPA

To an 500-mL round bottom flask with a mechanical stirrer and reflux condenser was added cis-hexahydrophthalic anhydride (15.4 g, 100 mmol), water (200 mL), and sodium hydroxide (16 g, 400 mmol) and the mixture heated to 50° C. After stirring with heat for 2 hours, a solution of strontium chloride hexahydrate (26.7 g, 168 mmol) was added and a white flocculate appeared immediately. The white product was collected by suction filtration, washed with copious amounts of water, and dried in a vacuum oven overnight at 110° C. The dry weight was 25 grams (97% yield) with a melting point in excess of about 400° C. The IR and NMR spectra were consistent with the expected product.

EXAMPLE 3 cis-Dilithium HHPA

To a 1-L 3-necked round bottom flask fitted with a reflux condenser, mechanical stirrer, and thermometer was added water (300 mL), lithium hydroxide monohydrate (17.7 g, 421 mmol), and cis-hexahydrophthalic anhydride (30.8 g, 200 mmol). After heating at reflux for 3 hours, the reaction mixture was cooled and then poured into acetone (500 mL). No precipitate formed, and the solvents were removed by rotary evaporation to give a white powder. The powder was washed on a filter with 50 mL of cold water, and the solid was dried in a vacuum oven at 85° C. overnight. The dry weight as about 37 grams (100%), with a melting point greater than about 350° C. IR and NMR analysis were consistent with that of the expected product.

EXAMPLE 4 cis-Monobasic Aluminum HHPA

To a 500-mL round bottom flask with a mechanical stirrer was added cis-disodium HBPA (10 g, 46.2 mmol) and water (100 mL). When homogeneity was obtained, a solution of aluminum sulfate (15.4 g, 23 mmol) in water (100 mL) was added, at which time a white flocculate formed immediately. After stirring at 50° C. for 30 minutes, the pH was adjusted to 9, the white solid was collected-via suction filtration, washed with water (200 mL), and dried in a vacuum oven overnight at 100° C. The dry weight equaled 8.7 grams (88%) with a melting point of greater than about 400° C. IR and NMR analysis were consistent with that of the expected structure.

EXAMPLE 5 cis-Disodium HHPA

To a 250-mL Erlenmeyer flask with a magnetic stirrer was added water (100 mL), sodium hydroxide (10.38 g, 260 mmol), and cis-hexahydrophthalic anhydride (20 g, 130 mmol). The reaction mixture was stirred at room temperature until homogeneous, at which time a slight exotherm was observed. After stirring for three hours, the solution was poured into acetone (2 L), and the white solid collected via suction filtration. Drying in a vacuum oven at 110° C. gave 20.9 g (74%) as a white powder, mp>350° C. IR and NMR analyis were consistent with that of the expected product.

EXAMPLE 6 cis-Magnesium HHPA

To a 500-mL Erlenmeyer flask with a magnetic stirring bar was added water (200 mL) and cis-disodium HHPA (20 g, 92.4 mmol) with stirring. After homogeneity was obtained, a solution of magnesium sulfate (11.1 g, 92.4 mmol) in water (100 mL) was slowly added. After stirring for 3 hours, the solvent was removed by rotary evaporation, affording a white solid. The sodium sulfate by-product was removed by sonicating the powder in methanol (300 mL), filtering, and drying in a vacuum oven at 110° C. overnight. Dry weight=17 grams (95%), mp>400° C. IR and NMR analysis were consistent with that of the expected product.

EXAMPLE 7 cis-Barium HHPA

To a 500-mL round bottom flask with a mechanical stirrer was added cis-hexahydrophthalic anhydride (15.4 g, 100 mmol), water (200 mL), and sodium hydroxide (16 g, 400 mmol). When homogeneity was obtained, a solution of barium chloride (20.8 g, 100 mmol) in water (50 mL) was added, at which time a white flocculate formed immediately. After stirring for 30 minutes, the white solid was collected via suction filtration, washed with water (100 mL), and dried in a vacuum oven overnight at 115° C. Dry weight=30.7 grams (99%), mp>400° C. IR and NMR analysis were consistent with that of the expected structure.

EXAMPLE 8 cis-Disilver HHPA

To a 500-mL round bottom flask with a mechanical stirrer was added cis-disodium HHPA (20 g, 92.4 mmol) and water (100 mL). When homogeneity was obtained, a solution of silver nitrate (31.39 g, 184.8 mmol) in water (100 mL) was added, at which time a white flocculate formed immediately. After stirring for 30 minutes, the white solid was collected via suction filtration, washed with water (200 mL), and dried in a vacuum oven overnight at 110° C. Dry weight=27.8 grams (78%), mp>400° C. IR and NMR analysis were consistent with that of the expected structure.

EXAMPLE 9 (COMPARATIVE)

cis-Dipotassium HHPA

To a 500-mL round bottom flask with a stir bar and reflux condenser was added cis-hexahydrophthalic anhydride (44 g, 285.4 mmol), water (200 mL), and potassium hydroxide (32 g, 570.8 mmol). When homogeneity was obtained, the solution was heated at reflux for 2 hours. The solution was cooled, and the solvent removed via rotary evaporation. The white solid was washed with acetone (250 mL), filtered and dried in a vacuum oven overnight at 100° C. Dry weight=59.8 grams (84%), mp>400° C. IR and NMR analysis were consistent with that of the expected structure. The sample proved to be too hygroscopic for testing in plastic (see Table 3 for hygroscopicity results).

EXAMPLE 10 (COMPARATIVE)

trans-Disodium HHPA

To a 1 -L Erlenmeyer flask with a magnetic stirrer was added acetone (500 mL) and trans-1,2-cyclohexanedicarboxylic acid 17.2 g (100 mmol) with stirring at room temperature. To this slurry was added a solution of sodium hydroxide (18 g, 450 mmol) in water (50 mL), at which time a thick white precipitate formed. After stirring a further 2 hours, the white solid was collected via suction filtration, washed with acetone (200 mL) and water (20 mL), and dried in a vacuum oven at 100° C. to give a white powder (dry weight=17.3 g, 80% yield), mp>400° C. IR and NMR analysis were consistent with that of the expected product.

Production of Nucleated Polyolefins with Inventive HHPA Salts

Before molding into polypropylene plaques, one kilogram batches of target polypropylene pellets were produced in accordance with the following table:

HOMOPOLYMER POLYPROPYLENE COMPOSITION TABLE

| Component | Amount |
|---|---|
| Polypropylene homopolymer (Basell Profax ® 6301) | 1000 g |
| Irganox ® 1010, Primary Antioxidant (from Ciba) | 500 ppm |
| Irgafos ® 168, Secondary Antioxidant (from Ciba) | 1000 ppm |
| Acid Scavenger (either Calcium Stearate, Lithium Stearate or DHT4-A) | as noted |
| Inventive HHPA salts | as noted |

The base resin (polypropylene homopolymer, hereinafter "HP") and all additives were weighed and then blended in a Welex mixer for 1 minute at about 1600 rpm. All samples were then melt compounded on a Killion single screw extruder at a ramped temperature from about 204° to 232° C. through four heating zones. The melt temperature upon exit of the extruder die was about 246° C. The screw had a diameter of 2.54 cm and a length/diameter ratio of 24:1. Upon melting the molten polymer was filtered through a 60 mesh (250 micron) screen. Plaques of the target polypropylene were then made through extrusion into an Arburg 25 ton injection molder. The molder was set at a temperature anywhere between 190 and 260° C., with a range of 190 to 240° C. preferred, most preferably from about 200 to 230° C. (for the Tables below, the standard temperature was 220° C.). The plaques had dimensions of about 51 mm×76 mm×3.00 mm (except for the plaques utilized as examples within Experimental Tables 1 and 2, which were 1.27 mm), and due to the mold exhibiting a mirror finish the resultant plaques exhibited a mirror finish as well. The mold cooling circulating water was controlled at a temperature of about 25° C. The same basic procedures were followed for the production of plaques of impact copolymer polypropylene (ICP, Table 2).

Nucleation capabilities were measured as polymer recrystallization temperatures (which indicate the rate of polymer crystal formation provided by the presence of the nucleating additive) by melting the target plaques, cooling the plaques at a rate of about 20° C./minute, and recording the temperature at which polymer crystal reformation occurs ($T_c$). Crystallization half-time ($T_{1/2}$) is also a useful parameter which can determine to what extent a nucleating agent might reduce molding cycle times. In this test, the target plaques (ICP) were melted at 220° C., then quenched at a nominal rate of 200° C./min to 140° C., at which time the crystallization temperature at half height was measured. Control plaques without nucleating additives, as well as with NA-11 and NA-21 (from Asahi Denka) and sodium benzoate were also produced for comparative purposes for some or all of the above-noted measurements.

Flexural modulus testing (reported as 1% secant modulus) was performed on the above mentioned plaques using an MTS Sintech 1/S 40" instrument with a span of 44.8 mm, a fixed deflection rate of 11.95 mm/min, and a nominal sample width of 50 mm. Samples were prepared by cutting square sections (approximately 50 mm×50 mm) from the centers of the plaques in order to obtain an isotropically sized sample. In addition to testing the samples across the machine/flow direction as is customary (labeled as TD in the results Tables), samples were also tested by flexing across the transverse direction against the flow to measure stiffness in the weaker direction as well (labeled as MD in the results Tables) in order to examine the bi-directional stiffness of the plaques. Gardner impact resistance at room temperature was measured by ASTM D5420-98a on a BYK Gardner Impact tester using an 8 lb weight and no clamping. A Stiffness/Impact Balance (S/I) factor was calculated relative to the control non-nucleated resin in each case as follows:

$$S/I = \left( \sqrt{\frac{(FM)_{TD(nucleated)} \times (FM)_{MD(nucleated)}}{(FM)_{TD(control)} \times (FM)_{MD(control)}}} \right) \times \frac{GI_{nucleated}}{GI_{control}}$$

where FM is the flexural modulus as described above and GI is the Gardner Impact at room temperature as described above. This factor illustrates the solution to the conundrum posed by polypropylene resins, i.e. it is the product of the control-normalized stiffness and the control-normalized impact resistance. Therefore, a material exhibiting an improved stiffness/impact balance would have a larger S/I number, representative of the increased balance of properties.

Wide-angle x-ray diffraction was performed on each sample to assess the degree of orientation in the sample plaques. In order to get accurate measurements of the orientation and texture of the injection-molded parts, pole figures were calculated from the scattering intensities of the polypropylene (110) (2θ=14.45°) and (040) (2θ=17.20°) reflections as the parts were rotated about the machine axis. The method followed was similar to ASTM E81-96. However since this method is designed for texture analysis of metal films, the following modifications were made to study the texture of the injection molded polypropylene parts. The equipment used for the experiments was a Bruker AXS (Madison, Wis.) 4-circle diffractometer mounted on a rotating anode x-ray source generating CuKα radiation (λ=0.1542 nm). Columnar test specimens with cross section of about 2.87 mm×2.87 mm that had been cut from the molded plaques were aligned in the x-ray beam with the machine axis perpendicular to the x-ray beam and aligned with the φ axis of the instrument. Instrument angles were adjusted to 2θ=0°, ω=20°, χ=25° to obtain complete coverage of the diffraction space for both the (110) and (040) reflections in transmission mode. Data images were collected every 5° on φ with 3 second exposures to obtain the intensity data at each φ value as 2-dimensional data frames. The data were processed using the commercially available software package, GADDS (Bruker AXS, Madison, Wis.). Several software packages exist to carry out said pole figure analyses. To obtain a quantitative assessment of each reflection's [(110) and (040)] intensity distribution (texture), each frame in a run from a single compound was integrated over a specific range; 13.2°–15.2° with a linear background subtraction based on the background scattering at the low 2θ (13.0°–13.2°) and high 2θ (15.2°–15.4°) ends for the (110) peak and 16.2°–17.9° with a linear background subtraction based on the background scattering at the low 2θ (16.0°–16.2°) and high 2θ (17.9°–18.1°) ends for the (040) peak. The resulting pole figure was interpolated using the GADDS software, and smoothed based on the crystallographic symmetry (2/m). Lastly, the Herman's orientation indices (HOI) were calculated within the GADDS software thus obtaining the quantitative relationships between the directionality of each [(110) and (040)] reflection and the three part directions: machine direction (MD), transverse direction (TD), and normal (thickness) direction (ND). By definition, the Herman's orientation indices run over the range –0.5 to 1.0 and are related to the relative inclination of the crystallographic axis being measured and the particular part direction it relates to, as determined by the formula $$HOI_{XD} = \frac{3\cos^2\Theta - 1}{2} \text{ where } XD = MD, TD, \text{ or } ND.$$

From this equation, one can obtain the angle $\theta_{XD}$ for each of the three directions MD, TD, ND. For example, if a crystallographic direction (e.g. the b-axis or (040) plane) of the polypropylene crystal becomes highly aligned along the ND, then $\theta_{ND}$ would approach 0° while $\theta_{MD}$ and $\theta_{TD}$ both align towards 90°. A completely random alignment to any axis would have a $\theta_{XD}$ of 54.76°. These data are listed in Table 2.

Based on these angles, and the additional knowledge that the (110) and (040) reflection planes are geometrically related to each other by an angle of 72.4° in a polypropylene crystal, one can construct the relationships between these planes and the part geometry and obtain a quantitative measure of the degree of alignment between the polypropylene crystals and the parts. Three functions were calculated $\text{Angle}_{MD} = \theta_{MD,110} - \theta_{MD,040}$; $\text{Angle}_{TD} = \theta_{TD,110} - \theta_{TD,040}$; $\text{Angle}_{ND} = \theta_{ND,110} - \theta_{ND,040}$. These three relationships give a quantitative description of the relationships between the (110) and (040) reflections and easily define a range of b-axis orientations in relevant samples. Furthermore, if one subtracts the orientation of the control, non-nucleated resin from each sample one obtains a processing independent measurement of the effects of the nucleating agents (Relative Angle).

Tables 1 and 2 below show the performance data of several inventive HHPA salts in terms of peak crystallization temperature ($T_c$), percent haze, certain flexural modulus measurements (all temperatures listed below have a statistical error of +/–0.5° C., and all haze measurements have a statistical error of +/–0.25 haze units), and crystallization half-time (again with 1.27 mm plaques). The acid scavengers added were as follows: calcium stearate (CS), dihydrotalcite (commercial product from Kyowa Chemical known as DHT4-A), and lithium stearate (LS); such compounds were added in amounts of about 400–800 ppm within the target polypropylene compositions for formation of the test plaques, while the inventive HHPA salts were added at a concentration of 0.25% by weight unless otherwise noted. An asterisk (*) indicates no measurements were taken.

EXPERIMENTAL TABLE 1

Nucleation Performance of Inventive Salts in Homopolymer Polypropylene

| Plaque # | Nucleator Added (Ex. # from above) | Acid Scavenger Added | $T_c$ (° C.) | Haze (%) | 1% Secant Modulus, MPa (std. Dev.) |
|---|---|---|---|---|---|
| 10 | 1 | CS^ | 121 | 38 | 2209 (16.6) |
| 11 | 1 | DHT4-A^ | 122 | 53 | 2077 (8.3) |
| 12 | 1 | LS^ | 121 | 38 | 2190 (37.5) |
| 13 | 2 | CS | 120 | 43 | 2129 (17.9) |
| 14 | 2 | DHT4-A | 122 | 51 | 2060 (15.7) |
| 15 | 2 | LS | 120 | 37 | 2209 (3.3) |
| 16 | 3 | DHT4-A | 121 | 65 | 2023 (1.3) |
| 17 | 3 | LS | 121 | 61 | 1997 (25) |
| 18 | 4 | LS | 121 | 56 | 2022 (6.9) |
| 19 | 5 | CS | 121 | 34 | 2022 (7) |
| 20 | 5 | LS | 118 | 56 | 2049 (12.2) |
| 21 | 5 | DHT4-A | 121 | 38 | 1963 (17.3) |
| 22 | 6 | DHT4-A | 117 | 55 | 2026 (23.4) |
| 23 | 6 | LS | 114 | 67 | 1952 (18.3) |
| 24 | 7 | DHT4-A | 116 | 99 | 1892 (3.7) |
| 25 | 7 | CS | 115 | 78 | 1926 (4.2) |
| 26 (Comparatives) | 8 | DHT4-A | 119 | 58 | * |
| 27 | Sodium benzoate | None | 120 | 60 | * |
| 28 | Sodium benzoate | CS | 116 | 62 | * |
| 29 (control) | None | CS | 112 | 64 | 1691 (18) |

^ CS = Calcium Stearate at 800 ppm,
LS = Lithium Stearate at 800 ppm,
DHT4-A = Dihydrotalcite at 400 ppm.

Thus, the cyclic dicarboxylate salts exhibited consistently high peak crystallization temperatures, as well as lower haze and more consistent high flexural modulus measurements than the comparative examples, particularly upon the introduction of highly desirable acid scavengers.

EXPERIMENTAL TABLE 2

Crystallization Half-Time of Example 1 vs. Comparative Examples in ICP

| Plaque # | Additives | Additive Concentration (ppm) | Cryst. Temp (DSC peak max.) | Crystallization Half-time (minutes) |
|---|---|---|---|---|
| 28 (comparative) | Control (None) | — | 115 | — |
| 29 | Example 1 | 2500 | 123 | 4.81 |
| 30 (comparative) | DMDBS | 2500 | 126 | 2.83 |
| 31 (comparative) | NA-11 | 1000 | 126 | 2.52 |
| 32 (comparative) | Sodium Benzoate | 2500 | 123 | 8.05 |
| 33 (comparative) | NA-21 | 2200 | 123 | 10.44 |

Thus, the inventive calcium HHPA salt exhibited acceptable peak crystallization temperatures and crystallization half-time measurements as compared the prior art nucleators.

Hygroscopicity Testing

These tests were carried out on the milled products to give adequate surface area for moisture uptake. Two grams of each example were spread out on a watch glass and weighed immediately after drying in a vacuum oven. The samples were then placed in a controlled humidity (65%) environment and the weight was taken each day for 7 days. The percent weight gain was defined as the percent moisture uptake at 7 days. Table 3 below summarizes the results:

EXPERIMENTAL TABLE 3

Hygroscopicity of Compounds

| Nucleator Example # | % Water Absorbed |
|---|---|
| 1 | 0.20 |
| 5 | 0.45 |
| sodium benzoate (Comparative) | 1.20 |
| 9 (Comparative) | 38.00 |
| 10 (Comparative) | 40.00 |

It is clear from the above data that the inventive compound from Example 1 exhibits greatly reduced hygroscopicity over that of the prior art as well as a higher molecular weight Group I metal salt (dipotassium). Additionally, the cis-disodium HHPA compound exhibited far reduced hygroscopicity than the trans-disodium HHPA. The term "low hydrogroscopicity" for purposes of this invention thus indicates a % water absorbed of at most 5%, preferably at most 2%, and more preferably below 1%, and most preferably below 0.5%.

Production of Nucleated PET with Example 1 (5000 ppm)

Additives were compounded with a C. W. Brabender Torque Rheometer at 5000 ppm into Shell Cleartuff™ 8006 PET bottle grade resin having an IV of 0.80. All resin was dried to less than 20 ppm water. Samples were taken, pressed, and rapidly cooled into 20–40 mil films. All samples were dried at 150° C. under vacuum for 6 h prior to analysis. 5 mg samples were analyzed under nitrogen on a Perkin Elmer System 7 differential scanning calorimeter using a heating and cooling rate of 20° C./min. $T_c$ data was collected after holding the samples at 290° C. for 2 min. before cooling. The data is shown below in Table 4:

EXPERIMENTAL TABLE 4

Polymer Crystallization Temperature of Example 1 in PET

| Sample | $T_c$ (° C.) |
|---|---|
| Control | 155 |
| Nucleator Example 1 | 180 |

Thus, the inventive compound of Example 1 exhibited much improved nucleation of polyester over the control with no nucleator compound.

Further Physical Property Measurements in Polypropylene

Experimental Table 5 shows the performance of the example compounds in physical property performance (within 3 mm thick plaques; the same thickness plaques were utilized for the remaining Experimental Table examples as well). The inventive material displays an increased $T_c$, improved haze, improved bi-directional stiffness, isotropic stiffness as measured by the ratio between $FM_{TD}$ and $FM_{MD}$, improved impact resistance, and improved S/I ratio. Although other comparative examples display some of these properties, none of the comparative examples simultaneously display them all. For example, the inventive material displays a high flexural modulus such as one would expect when using a filler (e.g. talc) yet a comparable stiffness to 5% talc is obtained by using only about 0.12% of the inventive "b-axis" nucleator. One might expect to be able to use a lower level of the inventive nucleator than the filler and still obtain similar stiffness properties. This effect should allow for use of lighter part weight by removal of filler and/or thin-gauging the part such as might be beneficial for cost-savings of material and/or in weight sensitive applications such at automotive applications. Additionally, the stiffness is bi-directional when comparing the flexural modulus ratios of the additives and comparing to their deviation from ideality (i.e. 1.000). The inventive nucleator deviates by only 0.008 while no other compound (except Millad 3988) behaves to such an isotropic degree, having a ratio that deviates from ideality by 0.015–0.069 with the highest deviations occurring with the filled systems. Furthermore, quite unexpectedly, the impact resistance of the inventive material is significantly improved over that of the control resin as well as all of the other materials used to nucleate the resin. For example, the highest impact resistance obtained for the additives is with the inventive material that has an impact resistance of 9.5 J compared to 1.4 J for the control resin and 5.3 J for the best comparative example, Millad® 3988 from Milliken & Company. None of the talc samples display good impact resistance. Because the inventive material displays both high stiffness and high impact resistance, its S/I balance is significantly enhanced over the control, 8.15 vs. 1.00 for the control (by definition). The highest comparative sample has an S/I of 4.00 for the Millad 3988 and none of the talc samples are significantly improved over the control resins.

Experimental Tables 6 and 7 illustrate the differences in the pole figure orientation functions obtained from wide-angle x-ray scattering. As can be seen from the data, the improvements in the physical properties discussed in Experimental Table 5 arise from improvements in the "b-axis" orientation with the inventive material having the characteristic features of b-axis orientation. B-axis orientation is maximized as the b-axis of the polypropylene crystals become aligned with the normal part direction. This is observed in the WAXS data with a "Relative Angle$_{ND}$" that is greater than 0°, preferably greater than 10°, and more preferably greater than 15°; a "Relative Angle$_{TD}$" that is less than 0°, preferably less than 5°, most preferably less than 10°, and a "Relative Angle$_{TD}$" that is less than 0°. Experimental Table 8 shows the same measurements for different cyclic dicarboxylate salt nucleating agents.

EXPERIMENTAL TABLE 5

Comparison of Physical Properties of Commercially Available Nucleating Agents

| # | Additive (*) | Level (%) | Haze (%) | Tc (° C.) | 1% Secant Modulus (TD) (MPa) | 1% Secant Modulus (MD) (MPa) | Ratio | Gardner S/I Impact (RT) (J) | |
|---|---|---|---|---|---|---|---|---|---|
| 30 | none | — | 99.2 | 116.8 | 1690 | 1728 | 0.978 | 1.4 | 1.00 |
| 31 | Ex. 1 | 0.12 | 75.7 | 119.8 | 2044 | 2060 | 0.992 | 9.5 | 8.15 |
| 32 | NaBz | 0.12 | 87.2 | 120.3 | 1943 | 1866 | 1.035 | 1.3 | 1.04 |
| 33 | HPN-68 | 0.12 | 75.4 | 127.0 | 1844 | 1873 | 0.985 | 2.0 | 1.55 |
| 34 | NA-11 | 0.12 | 62.7 | 124.6 | 1943 | 1913 | 1.016 | 0.9 | 0.73 |
| 35 | Zn-Gly | 0.12 | 84.9 | 124.7 | 1878 | 1916 | 0.980 | 3.2 | 2.54 |
| 36 | DMDBS | 0.12 | 85.1 | 120.7 | 1813 | 1799 | 1.008 | 5.3 | 4.00 |
| 37 | NA-21 | 0.12 | 70.9 | 122.2 | 1961 | 1890 | 1.038 | 3.9 | 3.14 |
| 38 | Talc | 0.1 | 97.0 | 115.4 | 2001 | 1934 | 1.035 | 1.9 | 1.56 |
| 39 | Talc | 0.2 | 97.2 | 116.3 | 2033 | 1953 | 1.041 | 1.4 | 1.16 |
| 40 | Talc | 0.5 | 97.9 | 116.7 | 2051 | 2003 | 1.024 | 1.0 | 0.85 |
| 41 | Talc | 1.0 | 98.7 | 117.4 | 2087 | 2017 | 1.035 | 1.0 | 0.86 |
| 42 | Talc | 5.0 | 100 | 117.6 | 2159 | 2103 | 1.027 | 0.9 | 0.80 |
| 43 | Talc | 10 | 100 | 118.7 | 2475 | 2373 | 1.043 | 0.5 | 0.51 |
| 44 | Talc | 25 | 100 | 119.6 | 2845 | 2662 | 1.069 | 0.3 | 0.35 |

(*) NaBz = sodium benzoate; HPN-68 = di-sodium bicyclo[2.2.1]heptane-cis-2,3- dicarboxylate; NA-11 = sodium 2,2'-methylene-bis-(4,6-di-tert-butylphenyl)phosphate; Zn- Gly = Zinc Glycerolate; NA-21 = monobasic aluminum/lithium 2,2'-methylene-bis-(4,6-di-tert-butylphenyl)phosphate; DMDBS = 1,3-O-2,4-bis(3,4-dimethylbenzylidene) sorbitol It is evident that the Ca HHPA salt provided a far higher stiffness to impact balance ratio than for any other nucleating additive tested within the test homopolymer.

EXPERIMENTAL TABLE 6

Comparison of XRD Properties of Commercially Available Nucleating Agents

| # | Additive | Level (%) | HKL | HOI(MD) | HOI (TD) | HOI(ND) | $\theta_{MD}(°)$ | $\theta_{TD}(°)$ | $\theta_{ND}(°)$ |
|---|---|---|---|---|---|---|---|---|---|
| 45 | none | — | 110 | 0.0052 | −0.0038 | −0.0014 | 54.5 | 54.9 | 54.8 |
|   |   |   | 040 | −0.1330 | 0.0729 | 0.0598 | 60.4 | 51.8 | 52.3 |
| 46 | Ex. 1 | 0.12 | 110 | 0.0376 | 0.0792 | −0.1170 | 53.2 | 51.6 | 59.6 |
|   |   |   | 040 | −0.1800 | −0.3120 | 0.4920 | 62.5 | 69.3 | 35.6 |
| 47 | NaBz | 0.12 | 110 | 0.0389 | −0.0116 | −0.0273 | 53.2 | 55.2 | 55.8 |
|   |   |   | 040 | −0.2650 | 0.1050 | 0.1590 | 66.7 | 50.6 | 48.5 |
| 48 | HPN-68 | 0.12 | 110 | 0.0039 | −0.0212 | 0.0173 | 54.6 | 55.6 | 54.0 |
|   |   |   | 040 | −0.1010 | 0.1750 | −0.0741 | 59.0 | 47.9 | 57.8 |
| 49 | NA-11 | 0.12 | 110 | 0.0359 | −0.0206 | −0.0152 | 53.3 | 55.6 | 55.4 |
|   |   |   | 040 | −0.2300 | 0.1300 | 0.1000 | 64.9 | 49.6 | 50.8 |
| 50 | Zn-Gly | 0.12 | 110 | 0.0119 | 0.0278 | −0.0397 | 54.3 | 53.6 | 56.4 |
|   |   |   | 040 | −0.1290 | −0.0514 | 0.1800 | 60.2 | 56.8 | 47.7 |
| 51 | DMDBS | 0.12 | 110 | −0.0002 | 0.0053 | −0.0051 | 54.7 | 54.5 | 58.7 |
|   |   |   | 040 | −0.0957 | 0.0360 | 0.0597 | 58.7 | 53.3 | 52.3 |
| 52 | NA-21 | 0.12 | 110 | 0.0382 | −0.0045 | −0.0337 | 53.2 | 54.9 | 56.1 |
|   |   |   | 040 | −0.2510 | 0.0590 | 0.1910 | 66.0 | 52.4 | 47.3 |
| 53 | Talc | 0.1 | 110 | 0.0586 | 0.0302 | −0.0888 | 52.4 | 53.5 | 58.4 |
|   |   |   | 040 | −0.1990 | −0.0434 | 0.2430 | 63.4 | 56.5 | 45.3 |
| 54 | Talc | 0.2 | 110 | 0.0612 | 0.0356 | −0.0968 | 52.3 | 533.3 | 58.8 |
|   |   |   | 040 | −0.2040 | −0.0612 | 0.2650 | 63.6 | 57.3 | 44.4 |
| 55 | Talc | 0.5 | 110 | 0.0641 | 0.0441 | −0.1080 | 52.2 | 53.0 | 59.3 |
|   |   |   | 040 | −0.2190 | −0.0610 | 0.2800 | 64.4 | 57.2 | 43.9 |
| 56 | Talc | 1.0 | 110 | 0.0677 | 0.0497 | −0.1170 | 52.0 | 52.7 | 59.6 |
|   |   |   | 040 | −0.2320 | −0.0635 | 0.2950 | 65.0 | 57.4 | 43.3 |
| 57 | Talc | 5.0 | 110 | 0.0671 | 0.0532 | −0.1200 | 52.1 | 52.6 | 59.8 |
|   |   |   | 040 | −0.2340 | −0.0781 | 0.3120 | 65.1 | 58.0 | 42.6 |
| 58 | Talc | 10 | 110 | 0.0708 | 0.0662 | −0.1370 | 51.9 | 52.1 | 60.5 |
|   |   |   | 040 | −0.2610 | −0.1030 | 0.3640 | 66.5 | 59.0 | 40.6 |

EXPERIMENTAL TABLE 6-continued

Comparison of XRD Properties of Commercially Available Nucleating Agents

| # | Additive | Level (%) | HKL | HOI(MD) | HOI (TD) | HOI(ND) | $\theta_{MD}(°)$ | $\theta_{TD}(°)$ | $\theta_{ND}(°)$ |
|---|---|---|---|---|---|---|---|---|---|
| 59 | Talc | 25 | 110 | 0.0528 | 0.1040 | −0.1570 | 52.6 | 50.6 | 61.4 |
|  |  |  | 040 | −0.2450 | −0.0807 | 0.3250 | 65.6 | 58.1 | 42.1 |

These measurements were then utilized to extrapolate the relative angles in relation to b-axis nucleation in the following Tables.

EXPERIMENTAL TABLE 7

Comparison of XRD Properties of Commercially Available Nucleating Agents

| # | Additive | Level (%) | Carbon (%) | Angle (MD) | Angle (TD) | Angle (ND) | Relative Angle(MD) | Relative Angle(TD) | Relative Angle(ND) |
|---|---|---|---|---|---|---|---|---|---|
| 60 | none | — | 0.0 | −5.8 | 3.1 | 2.4 | 0.0 | 0.0 | 0.0 |
| 61 | Ex. 1 | 0.12 | 45.7 | −9.3 | −17.7 | 24.1 | −3.4 | −20.7 | 21.6 |
| 62 | NaBz | 0.12 | 58.3 | −13.5 | 4.6 | 7.4 | −7.7 | 1.6 | 4.9 |
| 63 | HPN-68 | 0.12 | 47.4 | −4.4 | 7.7 | −3.8 | 1.5 | 4.7 | −6.2 |
| 64 | NA-11 | 0.12 | 68.5 | −11.6 | 6.0 | 4.6 | −5.8 | 2.9 | 2.1 |
| 65 | Zn-Gly | 0.12 | 23.8 | −5.9 | −3.2 | 8.7 | −0.1 | −6.3 | 6.2 |
| 66 | DMDBS | 0.12 | 69.5 | −4.0 | 1.2 | 2.6 | 1.8 | −1.8 | 0.1 |
| 67 | NA-21 | 0.12 | 70.7 | −12.8 | 2.5 | 8.9 | −6.9 | −0.5 | 6.4 |
| 68 | Talc | 0.1 | 0.0 | −11.0 | −3.0 | 13.2 | −3.9 | −6.1 | 9.5 |
| 69 | Talc | 0.2 | 0.0 | −11.3 | −4.0 | 14.3 | −4.3 | −7.0 | 10.7 |
| 70 | Talc | 0.5 | 0.0 | −12.2 | −4.3 | 15.4 | −5.1 | −7.3 | 11.8 |
| 71 | Talc | 1.0 | 0.0 | −13.0 | −4.6 | 16.4 | −5.9 | −7.7 | 12.7 |
| 72 | Talc | 5.0 | 0.0 | −13.0 | −5.4 | 17.2 | −6.0 | −8.4 | 13.5 |
| 73 | Talc | 10 | 0.0 | −14.6 | −6.9 | 19.9 | −7.5 | −10.0 | 16.3 |
| 74 | Talc | 25 | 0.0 | −13.0 | −7.5 | 19.3 | −6.0 | −10.5 | 15.7 |

The relative angle (ND) for the Ca HHPA nucleating agent is far higher than any of the other additives indicating the ability to induce b-axis nucleation to a degree heretofore unforeseen.

EXPERIMENTAL TABLE 8

Comparison of XRD Properties of Related HHPA Derivatives

| # | Additive | Level (%) | Carbon (%) | Angle (MD) | Angle (TD) | Angle (ND) | Relative Angle(MD) | Relative Angle(TD) | Relative Angle(ND) |
|---|---|---|---|---|---|---|---|---|---|
| 75 | none | — | 0.0 | −17.4 | 3.9 | 10.8 | 0.0 | 0.0 | 0.0 |
| 76 | Ex. 1 | 0.25 | 45.7 | −22.7 | −20.7 | 39.3 | −5.4 | −24.6 | 28.5 |
| 77 | Ex. 5 | 0.25 | 44.4 | −20.9 | −12.8 | 30.2 | −3.4 | −16.7 | 19.4 |
| 78 | Ex. 10 | 0.25 | 44.4 | −19.7 | −7.8 | 24.4 | −2.4 | −11.7 | 13.5 |
| 79 | Ex. 3 | 0.25 | 52.2 | −16.1 | −2.9 | 27.0 | 1.3 | −6.9 | 6.2 |
| 80 | Ex. 6 | 0.25 | 49.4 | −18.9 | 2.0 | 13.9 | −1.5 | −1.9 | 3.1 |
| 81 | Ex. 4 | 0.25 | 44.9 | −17.0 | −5.4 | 20.1 | 0.3 | −9.3 | 9.3 |

Thus, the ability for cyclic dicarboxylates to induce an excellent b-axis nucleation within polypropylene, in particular at very low levels of addition therein, is highly unexpected and beneficial to provide excellent physical properties.

Having described the invention in detail it is obvious that one skilled in the art will be able to make variations and modifications thereto without departing from the scope of the present invention. Accordingly, the scope of the present invention should be determined only by the claims appended hereto.

That which is claimed is:

1. An organic nucleating agent which induces b-axis orientation within a test homopolymer polypropylene formulation to a degree in which a relative angle (ND) of greater than 13.5 is detected, wherein the unnucleated test homopolymer polypropylene formulation exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 kpi, an Izod impact strength of about 0.67 ft-lb/in, and a deflection temperature at 0.46 mPa of about 93°, and wherein said formulation comprising said combination is extruded then molded into plaques having dimensions of about 51 mm×76 mm×3.00 mm, wherein the total amount of said organic nucleating agent present within said test homopolymer is at most 0.25% by weight, and wherein said nucleating agent is a compound conforming to Formula (I)

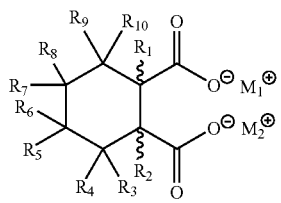

wherein $M_1$ and $M_2$ are the same or different, or $M_1$ and $M_2$ are combined to form a single moiety, and are selected from at least one Group I or Group II metal cation, and wherein $R_1$, $R_2$, $R_3$, $R_4$, $R_5$, $R_6$, $R_7$, $R_8$, $R_9$, and $R_{10}$ are either the same or different and are individually selected from the group consisting of hydrogen, $C_1$–$C_9$ alkyl, hydroxy, $C_1$–$C_9$ alkoxy, $C_1$–$C_9$ alkyleneoxy, amine, and $C_1$–$C_9$ alkylamine, halogens, and phenyl.

2. A thermoplastic composition comprising the organic nucleating agent as defined in claim 1.

3. The thermoplastic composition of claim 2 wherein said thermoplastic is a polyolefin.

4. The polyolefin composition of claim 3 wherein said polyolefin is a polypropylene.

5. An organic nucleating agent which induces a stiffness to impact balance ratio (S/I) of greater than 4.5 within a test homopolymer polypropylene formulation, wherein the unnucleated test homopolymer polypropylene formulation exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93°, and wherein said formulation comprising said combination is extruded then molded into plaques having dimensions of about 51 mm×76 mm×3.00 mm, wherein the total amount of said organic nucleating agent present within said test homopolymer is at most 0.25% by weight, and wherein said nucleating agent is a compound conforming to Formula (I)

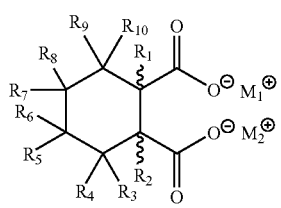

wherein $M_1$ and $M_2$ are the same or different, or $M_1$ and $M_2$ are combined to form a single moiety, and are selected from at least one Group I or Group II metal cation, and wherein $R_1$, $R_2$, $R_3$, $R_4$, $R_5$, $R_6$, $R_7$, $R_8$, $R_9$, and $R_{10}$ are either the same or different and are individually selected from the group consisting of hydrogen, $C_1$–$C_9$ alkyl, hydroxy, $C_1$–$C_9$ alkoxy, $C_1$–$C_9$ alkyleneoxy, amine, and $C_1$–$C_9$ alkylamine, halogens, and phenyl.

6. A thermoplastic composition comprising the organic nucleating agent defined in claim 5.

7. The thermoplastic composition of claim 6 wherein said thermoplastic is a polyolefin.

8. The polyolefin composition of claim 7 wherein said polyolefin is a polypropylene.

9. A polypropylene article comprising at least one cyclic dicarboxylate nucleating agent, wherein said polypropylene comprises at least a fraction of homopolymer and exhibits a b-axis orientation, wherein said at least one nucleating agent exhibits very low hygroscopicity, and wherein said at least one nucleating agent induces a crystallization temperature of at least 116° C. within a test homopolymer propylene formulation, wherein the unnucleated test homopolymer propylene formulation exhibits a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93°, and wherein said formulation comprising said combination is extruded then molded into plaques having dimensions of about 51 mm×76 mm×3.00 mm, wherein said peak crystallization temperature is measured by differential scanning calorimetry in accordance with a modified ASTM Test Method D3417-99 at heating and cooling rates of 20° C./minute, wherein the total amount of said organic nucleating agent present within said test homopolymer is at most 0.25% by weight, and wherein said nucleating agent is a compound conforming to Formula (I)

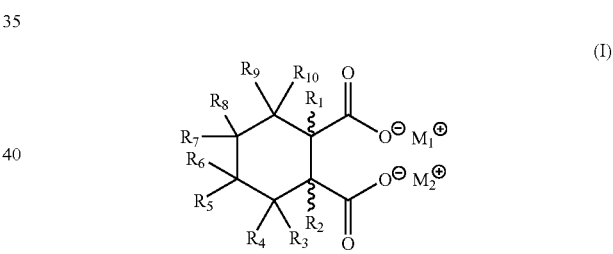

wherein $M_1$ and $M_2$ are the same or different, or $M_1$ and $M_2$ are combined to form a single moiety, and are selected from at least one Group I or Group II metal cation, and wherein $R_1$, $R_2$, $R_3$, $R_4$, $R_5$, $R_6$, $R_7$, $R_8$, $R_9$, and $R_{10}$ are either the same or different and are individually selected from the group consisting of hydrogen, $C_1$–$C_9$ alkyl, hydroxy, $C_1$–$C_9$ alkoxy, $C_1$–$C_9$ alkyleneoxy, amine, and $C_1$–$C_9$ alkylamine, halogens, and phenyl.

10. The article of claim 9 wherein each of $R_1$, $R_2$, $R_3$, $R_4$, $R_5$, $R_6$, $R_7$, $R_8$, $R_9$, and $R_{10}$ are hydrogen and $M_1$ and $M_2$ are combined as a single calcium ion.

* * * * *